United States Patent [19]

Cathignol et al.

[11] Patent Number: 5,015,929
[45] Date of Patent: May 14, 1991

[54] PIEZOELECTRIC DEVICE WITH REDUCED NEGATIVE WAVES, AND USE OF SAID DEVICE FOR EXTRACORPOREAL LITHOTRITY OR FOR DESTROYING PARTICULAR TISSUES

[75] Inventors: Dominique Cathignol, Genas; Bernard Lacruche, Lyons; Jean-Louis Mestas, Chassieu, all of France

[73] Assignees: Technomed International, S.A., Paris; Institut National de la Sante et de la Recherche Medical (Inserm), Lyons, both of France

[21] Appl. No.: 449,503

[22] Filed: Dec. 1, 1989

Related U.S. Application Data

[63] Continuation of Ser. No. 197,987, May 24, 1988, abandoned.

[30] Foreign Application Priority Data

Sep. 7, 1987 [FR] France .................................. 87 12385

[51] Int. Cl.⁵ .......................................... H01L 41/08
[52] U.S. Cl. ..................................... 310/335; 310/334
[58] Field of Search ............... 310/322, 323, 334–337, 310/366, 369; 128/660

[56] References Cited

U.S. PATENT DOCUMENTS

| | | | |
|---|---|---|---|
| 2,169,304 | 8/1939 | Tournier | 310/335 X |
| 3,656,012 | 4/1972 | Dixon | 310/334 |
| 3,879,698 | 4/1975 | Pepper | 310/334 |
| 3,939,467 | 2/1976 | Cook et al. | 310/334 X |
| 4,350,917 | 9/1982 | Lizzi et al. | 310/335 X |
| 4,395,652 | 7/1983 | Nakanishi | 310/334 |
| 4,401,910 | 8/1983 | Beerman | 310/369 |
| 4,439,847 | 3/1984 | Massa | 310/337 X |
| 4,445,207 | 4/1984 | Sternberg | 310/335 X |
| 4,576,048 | 3/1986 | Glenn | 310/335 X |
| 4,582,065 | 4/1986 | Adams | 310/335 X |
| 4,639,904 | 1/1987 | Riedlinger | 310/335 X |
| 4,670,683 | 6/1987 | Hoen | 310/335 X |
| 4,865,042 | 9/1989 | Umemura et al. | 310/335 X |
| 4,890,268 | 12/1989 | Smith et al. | 319/334 X |

FOREIGN PATENT DOCUMENTS

| | | |
|---|---|---|
| 0289382 | 11/1988 | European Pat. Off. . |
| 2567394 | 1/1986 | France . |
| 2571635 | 4/1986 | France . |
| 2579355 | 9/1986 | France . |

*Primary Examiner*—Mark O. Budd
*Attorney, Agent, or Firm*—Schechter, Brucker & Pavane

[57] ABSTRACT

The invention relates to a device generating ultrasonic waves focused in a focal point. Said generator device comprises a plurality of transducer elements arranged externally on a support means for focusing into a focal point, such as a circular dome, and is characterized in that the transducer elements are divided into at least two groups of transducer elements, of which the resonance frequency differs in such a way that the principal positive ultrasonic waves produced by each group add up together and the positive and negative secondary ultrasonic waves are at least partly cancelled, thus reducing significantly the negative waves. This device can be advantageously used for extracorporeal lithotripsy.

18 Claims, 3 Drawing Sheets

PIEZOELECTRIC DEVICE WITH REDUCED NEGATIVE WAVES, AND USE OF SAID DEVICE FOR EXTRACORPOREAL LITHOTRITY OR FOR DESTROYING PARTICULAR TISSUES

This is a continuation of U.S. application Ser. No. 07/197,987 filed May 24, 1988 now abandoned.

The present invention essentially relates to a piezoelectric device with reduced negative waves, and to the use of such device for extracorporeal lithotripse or for the destruction of particular tissues.

BACKGROUND OF THE INVENTION

Conventionally, a piezoelectric generator is essentially composed of one, or several or a very large number of piezoelectric elements preferably arranged on a circular dome permitting the focusing of all the minute waves created by each elementary particle constituting the transducer or transducers (see for example the document "Ultrasonics", vol. 5, of April 1967, pages 105–112; P. P. LELE).

Another device for generating ultrasonic waves focused in one point has also been described, which device comprises a plurality of transducer elements of piezoelectric type arranged externally on a circular dome, as well as its use for therapeutical purposes, for example for producing controlled ocular lesions (see article by COLEMAN, in the American Journal of Ophthalmology 86:185–192, 1978). COLEMAN also describes the paraxial presence of a diagnosis transducer.

Experience has proved that the quality of the focusing or in other words, the volume of the focal spot, will be smaller as the filling coefficient is near to 1 and as the opening defined by the angle of the circular dome is high.

It is further known that the shape of the wave at the focal point is identical or near-identical and in any case closely dependent on the shape of the wave emitted at the level of the piezoelectric transducer. In the case of a transducer with one face in contact with the water and the other face in contact with the air (the simplest mounting possible and the most used), the generated wave, after an electric pulse, is in the form of a damped sine wave presenting positive and negative waves.

It has been found that negative waves are dangerous for the tissues because they can induce cavitation effects. (see article by COLEMAN et al. in "Ultrasound in Med. & Biol., Vol. 13, No. 2, pages 6914 76, 1987).

The prior art has already proposed to create waves called single-pole waves (document DE U.S. Pat. No. 34 25 992).

When the transducer is subjected to a very short pulse, it delivers a series of pulses, the front face emitting straight polarity waves while the rear face emits reversed polarity waves. The resultant emitted wave is of course the sum of those waves which is therefore now positive, now negative.

The object of the solution proposed in document DE U.S. Pat. No. 34 25 992 is to "separate" such positive and negatives waves. To do this, the rear face is cut irregularly in such a way that the waves reflected by said rear face are not focused or very incorrectly focused. The result is that the ratio of the positive wave to the negative wave increases as the focal point gets closer.

It should be noted that, with said solution, the second positive wave will also be incorrectly focused since it is due to the reflection of the first wave onto the rear face of the transducer.

It is also known to adapt the piezoelectric transducer by placing on the front face a material having an impedance ranging between the transducer impedance and that of the water used as transmission medium for transmitting the ultrasonic wave to the target situated at the focal point (see Vol. I, Part A of Physical Acoustics by MASON; Academic Press).

It is found then, firstly that the signal duration is very short, and secondly that the reached maximum pressure value is much higher as can be seen when comparing FIG. 1a (emission of non-adapted ultrasonic waves) and FIG. 1b (emission of ultrasonic waves by an adapted transducer).

Therefore, with the single-polar system such as proposed in DE U.S. Pat. No. 34 25 992, as only the first wave is focused and as regretfully said wave is always weak comparatively to the second and third waves, the ratio of the focused wave between an adapted transducer and a non-adapted transducer is in the region of a factor 10, but it is easy to realize that in the case of a non-adapted transducer, of which the rear face is not irregularly cut, the system generates a negative wave of amplitude equal to the positive wave.

In other terms, even with this solution, the negative wave is still present with an intensity such that it is capable of inducing cavitation effects dangerous for the tissues situated near to either the concretion or to the particular tissues to be destroyed.

SUMMARY OF THE INVENTION

It is therefore the object of the present invention to solve the aforesaid new technical problem by proposing a solution capable of reducing or eliminating completely the amplitude of the negative wave which is inherently present in the sine wave produced by any piezoelectric transducer.

It is also the object of the present invention to solve the new technical problem which arises by proposing a solution capable not only of reducing or eliminating completely the negative wave inherent in the sine wave produced by a piezoelectric transducer, but also of keeping to the same level the height of the peaks of the emitted wave, hence the pressure peak value comparatively to the prior art techniques, and in particular to the techniques of reduction of negative wave amplitude.

Such new technical problems have been solved satisfactorily for the first time by the present invention, on an industrial scale.

To this end, the present invention proposes a device for generating ultrasonic waves focused in a point having reduced negative waves, which device comprises a plurality of transducer elements of piezoelectric type, arranged externally on support means for focussing into a focal point, such as for example a circular dome device wherein said transducing elements are divided in at least two groups of transducer elements of which the resonance frequency differs in such a way that the principal positive ultrasonic waves produced by each group are added together, and the negative and positive secondary ultrasonic waves are at least partly cancelled out.

According to one particularly advantageous embodiment of the invention, the second group of transducer elements, or the other groups of transducer elements, has a resonance frequency equal or substantially equal to a multiple or a submultiple of the resonance frequency of the transducer elements of the first group.

According to a particular embodiment, the resonance frequency of the second group of transducer elements is equal or substantially equal to twice the resonance frequency of the first group of transducer elements.

According to another particularly advantageous embodiment, the transducer elements of each group are arranged in alternate fashion, so that the total surface occupied by the elements of each group is substantially identical.

According to yet another particular embodiment of the invention, all the transducers elements of the different groups are at the same distance, called focal distance, from the focal point. When the support means is a circular dome, the focal distance is preferably equal to the dome radius of curvature.

In the simpler case where the focal distance is the same for all the transducer elements of the different groups, a coinciding of the maximum pressure peaks is reached between the groups which have different resonance frequencies by an electronic ordering of each group of given frequency, this being achieved by sending pulses or a front of delayed or advanced voltage depending on the group being ordered with respect to the reference group, the time difference (delay or advance) being given by the following formula:

$$\Delta t = \lambda / 4 \, V,$$

in which:
V is the ultrasonic speed inside the medium (generally water), is the wavelength of the ordered group.

In the case where the support means is flat, it is possible to effect an electronic focusing as described in document DE-A-31 19 295.

According to yet another particular embodiment, when the support means is a circular dome, the distance set between the front face of the transducer elements of one given group and the focusing point, is different from the same distance to the focusing point of the other groups of different resonance frequency, the electric drive of all the groups is simultaneous so that the maximum pressure peaks coincide.

For example, the focal distance difference between the first group and the second group is about one quarter of a wavelength. Consequently, this compensation corresponds to the time compensation ($\Delta t$) when the focal distance is constant.

Moreover, when the resonance frequency of a given group is lower than the resonance frequency of the first group or reference group, the distance between the transducers and the focus point of said given group is greater than the distance between the transducers and the focus point of the reference group, this meaning that the transducer elements of said given group are offset with respect to the transducer elements of the reference group.

Similarly, if the resonance frequency is higher for the transducer elements of the given group, the distance between the transducers and the focal point is smaller than that between said focal point and the reference group of transducer elements, meaning that the transducer elements of said given group of higher resonance frequency are placed in front with respect to the transducer elements of the reference group.

According to another particularly advantageous embodiment, the device comprises a third group of transducer elements of which the resonance frequency is equal or substantially equal to four times the resonance frequency of the first group of transducer elements.

It is clear from anyone skilled in the art that the sum of the waves emitted by the transducer groups of different resonance frequency will give a resulting wave with a reduced amount of negative waves due to said combination, the principal positive waves adding up together while the negative waves are cancelled to a maximum, particularly by the secondary positive waves. It will be worth noting that the total sum of the principal positive waves produces a pressure peak identical to that produced in the conventional case in which only one resonance frequency is used for all the transducer elements.

The result is an effect which is totally unexpected and nonobvious to anyone skilled in the art who wants to destroy concretions lithotripsy or special tissues (surgical operations), or even to an expert in ultrasonic techniques.

BRIEF DESCRIPTION OF THE DRAWINGS

The invention will be more readily understood on reading the following description with reference to the accompanying drawings in which.

DETAILED DESCRIPTION OF PREFERRED EMBODIMENTS

Figure 2:
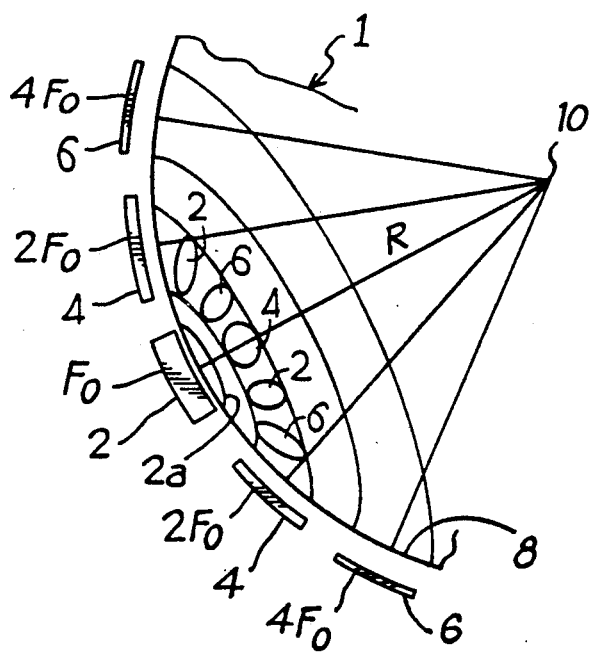
FIG. 2a illustrates a plan view of the internal face of the focusing dome according to a variant embodiment equipped with three groups of transducer elements of different resonance frequency, such as shown in FIG. 2.
FIG. 2b illustrates a plan view of the internal face of the focusing dome, according to a variant embodiment equipped with two groups of transducer elements of different frequency.
Figure 2A:
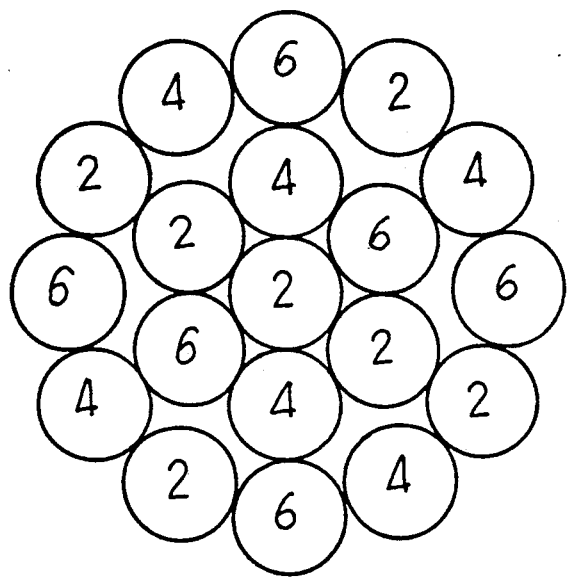
Figure 2B:
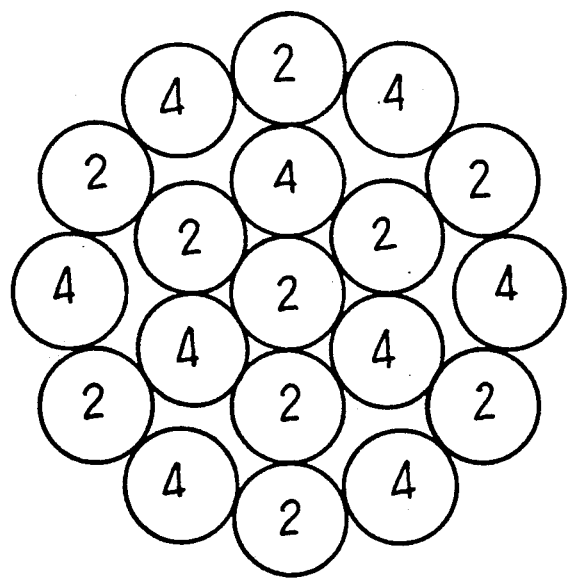

Referring first to FIGS. 2, 2a and 2b, these show a device for generating ultrasonic waves focused in one focal point, with a reduced amount of negative waves according to the present invention.

Said generator device designated by general reference 1 is of a type which is well known in ultrasonic generator technique, as partly summarized in the introductory part of the present description.

The illustrated generator device 1 comprises a plurality of piezoelectric type transducer elements 2, 4, 6, arranged externally on a support means 8 for focusing in one focal point 10. Said support means 8 is, in the illustrated case, a circular dome. This structure as well as the means for transmitting the pulses to the transducer elements, being known of anyone skilled in the art, will not be further described.

According to the present invention, the device is characterized in that the transducer elements are divided in at least two groups of transducer elements, i.e. as illustrated by way of example, a first group of transducer elements 2, a second group of transducer elements 4 and a third group of transducer elements 6, the resonance frequencies of which differ in such a way that the principal positive ultrasonic waves produced by each group are adding up and the secondary ultrasonic (positive or negative waves) are at least partly cancelled.

According to a particularly advantageous embodiment of the invention, the second group of transducer elements 4, or the other groups of transducer elements (4, 6), have a resonance frequency which is equal or substantially equal to a multiple or a submultiple of the resonance frequency of the transducer elements 2 of the first group, particularly to a multiple of said frequency.

According to another preferred embodiment, the resonance frequency of the second group of transducer elements 4 is equal or substantially equal to twice the resonance frequency $F_o$ of the first group of transducer elements 2.

According to another illustrated particular embodiment, the transducer elements of each group are arranged in alternated fashion, so that the total surface occupied by the transducer elements of each group is substantially identical, as can be seen clearly from FIGS. 2, 2a and 2b.

Taking for example FIG. 2a which illustrates a variant embodiment with three groups of transducer elements of different resonance frequency arranged in alternated fashion and designated respectively, the first group of transducer elements 2, the second group of transducer elements 4 and the third group of transducer elements 6. In the case of a third group of elements such as 6 being present, the resonance frequency of said transducer elements 6 is equal or substantially equal to four times the resonance frequency $F_o$ of the first group.

By way of example, said resonance frequency $F_o$ of the first group of transducer elements 2 is equal to 0.5 MHz.

Also in FIG. 2b, which illustrates another variant embodiment with two groups of transducer elements of different resonance frequency, the center position is for example occupied by a transducer element 2 of the first group whereas each peripheral sector is occupied alternately by transducer elements of the first group (element 2) and by transducer elements of the second group (element 4).

Also, to obtain different resonance frequencies, the thickness of the transducer elements 2 of the first group is twice or substantially twice the thickness of the transducer elements 4 of the second group and, in the case of the presence of a third group of transducer elements 6, it is equal or substantially equal to four times the thickness of the transducer elements 6 of the third group.

According to a simpler embodiment, all the transducer elements (2, 4, 6) of the different groups are at the same distance from the focal point 10, called focal distance.

When the support means is a circular dome, as illustrated in FIG. 2, the focal distance is preferably equal to the radius of curvature of the dome.

In the simplest case where the focal distance is the same for all the transducer elements (2, 4, 6) of the different groups, a coinciding of the maximum pressure peaks is obtained between the different groups having different resonance frequencies, by an electronic ordering on each group of given frequency, this being achieved by sending pulses or a front of voltage which is either delayed or advanced depending on the group being ordered with respect to the reference group, the time difference (delay or advance) being given by the formula:

$$\Delta t = \lambda/4 \, V$$

in which:

V is the ultrasonic speed inside the medium filling the dome, and generally constituted by water,
is the wavelength of the ordered group.

Anyone skilled in the art can thus know directly how to proceed with the electronic ordering of each group of frequency, in order to obtain the coinciding of the maximum pressure peak between the different groups at focal point 10.

For example, if the resonance frequency $F_o$ of the first group of piezoelectric elements 2 is 0.5 MHz and if the resonance frequency of the second group of piezoelectric elements 4 is twice that measurement, i.e. 1 MHz, the electronic ordering of the second group will be obtained with a delay of about one quarter of period T, i.e. 250 nsecs.

According to another possible embodiment, particularly when the support means is constituted by a circular dome, as illustrated in FIG. 2, the set distance between the front face of the transducer elements of the given group and focal point 10 is different from the same distance to said focal point of the other groups of different resonance frequency, this making it possible to achieve simultaneous electric or electronic ordering of all the groups so that the maximum pressure peaks coincide.

For example, the difference between the focal distances of the first and second groups is about one quarter of wavelength.

Such compensation is found to correspond to a time compensation ($\Delta t$) when the focal distance is constant.

It is therefore possible either to place all the transducer elements at an identical distance form the focal point 10 with a different electric ordering between the groups, while being synchronized in order to obtain coinciding maximum pressure peaks, or to modify the focal distance of the different groups, thereby performing a simultaneous ordering of all the transducer elements of the different groups.

Another suitable possibility according to the invention consists in using a flat support means as described in document DE-A-31 19 295, the focal distance being then different for transducer elements which may be of the same group, and in this case an electronic focusing is achieved as described hereinabove, this being perfectly obvious to anyone skilled in ultrasonic technology.

Figure 1A:
FIG. 1a illustrates the sine wave produced by a nonadapted piezoelectric transducer element, of resonance frequency $F_o$.
Figure 1B:
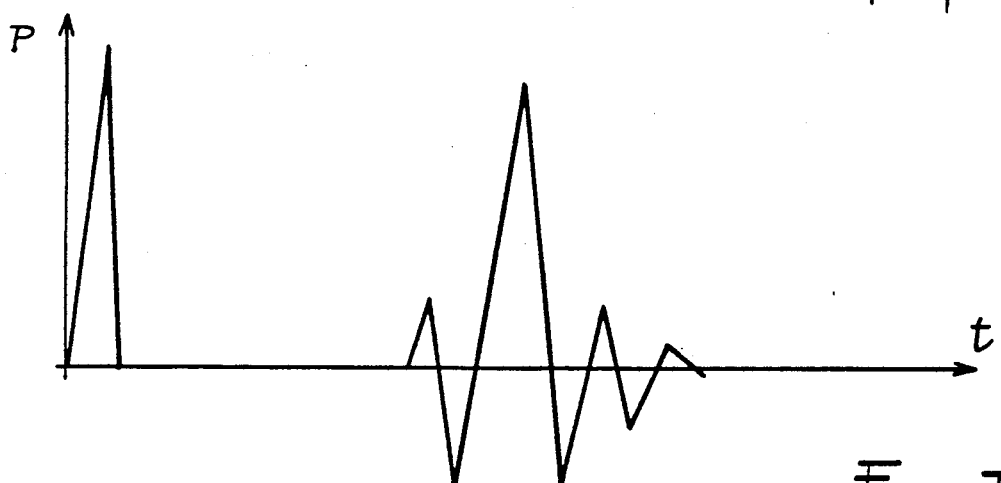
FIG. 1b illustrates the same piezoelectric transducer adapted by depositing a layer of epoxy resin on the emitting face, FIG. 2 diagrammatically illustrates a device according to the invention for generating ultrasonic waves, focused in one focus point, equipped with a focusing dome, in this example a circular dome.
Figure 3A:
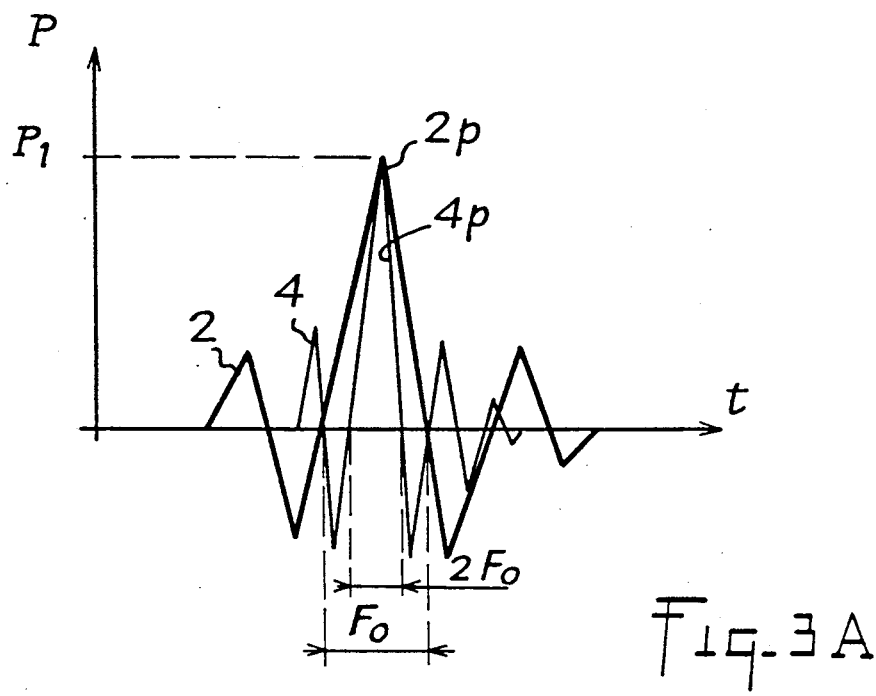
FIG. 3a illustrates individually the sine wave produced by the first group of resonance frequency $F_o$ and by the second group of resonance frequency $2F_o$.
Figure 3B:
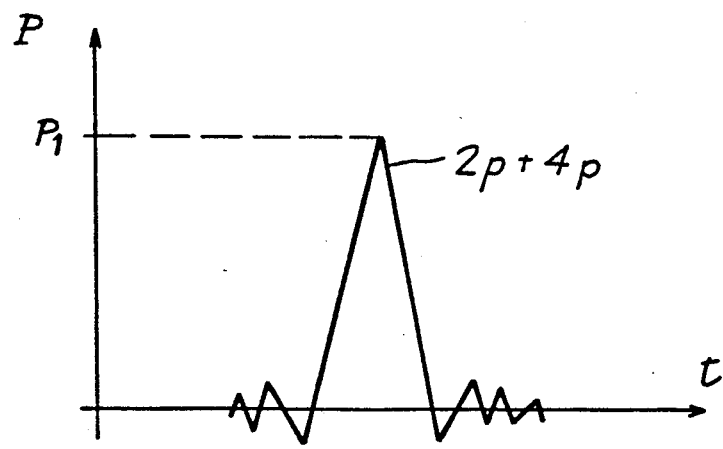
FIG. 3b illustrates the resultant wave, resulting from the sum of the two waves from the first group and from the second group, respectively.

With that combination of transducer elements of different resonance frequency, it is possible to reduce significantly the emission of negative waves while significantly increasing the pressure peak of the principal positive wave as illustrated in FIGS. 3a and 3b with respect to FIGS. 1a and 1b, explained hereafter.

For simplification purposes, FIG. 3a diagrammatically illustrates the wave emitted in time by the first group of transducer elements 2, the represented curve being also referenced 2, and by the second group of transducer elements 4, the curve then being referenced 4. It is observed that the principal positive wave 2p emitted by the first group of transducer elements 2 and the principal positive wave 4p emitted by the second group of transducer elements 4 have coinciding peaks, and consequently they will add up together to give a resultant principal positive wave, as illustrated in FIG. 3b and referenced 2p+4p.

On the contrary, the secondary positive waves and the secondary negative waves emitted by each group of transDucer elements 2, 4 are going to be at least partly cancelled, thus giving the curve of resultant wave of FIG. 3b.

It is found, as a result, that the negative wave has been significantly reduced. This effect will be amplified by the presence of the third group of transducer elements 6.

The amplitude of the negative wave will thus have been reduced to a level situated below the threshold at which said negative wave causes a cavitation effect capable of destroying or damaging the cells of tissues situated close to the target to be destroyed, such as a concretion, or a diseased tissue such as a tumor, contrary to what could be achieved with the generating device according to the prior art and comprising only one group of transducer elements with the same resonance frequency.

Moreover, and this is also a particularly unexpected and non-obvious effect for anyone skilled in the art, the resultant wave obtained according to the invention has a maximum pressure peak which is at least equal to the pressure peak obtained according to the prior art. The efficiency of destruction of the target present in the focus point is thus further improved by the practical presence of a single pressure peak, without any sensitive negative part.

Unquestionably, all the aforesaid determinant technical advantages have been obtained according to the invention.

The present invention obviously includes all the means which are the technical equivalents of the means described hereinabove.

For example, the piezoelectric transducer elements may be of any type, such as based on conventional titanate-zirconate or of any constitution enabling them to fulfill the required function. Similarly, the dimensions of the individual transducer elements as well as the radius of the circular dome can vary within a wide range. It is not even necessary for the transducer elements to be placed on a circular dome as focusing can be achieved electronically as taught for example in document DE-A-3 119 295, by changing the times of electric ordering of each group of transducer elements.

We claim:

1. A device for generating ultrasonic waves focused on one focal point, having reduced negative waves, comprising a plurality of transducer elements of piezoelectric type arranged on a support means for focusing at one focal point, wherein said transducer elements are divided into at least first and second groups of transducer elements having first and second resonance frequencies, respectively, which resonance frequencies are different, and wherein the second group of transducer elements has a resonance frequency which is equal or substantially equal to a multiple or a submultiple of the resonance frequency of the transducer elements of the first group such that the principal positive ultrasonic waves produced by each group are added and the positive and negative secondary ultrasonic waves are at least partly cancelled out.

2. Device as claimed in claim 1, wherein the resonance frequency of the second group of transducer elements is equal or substantially equal to twice the resonance frequency of the first group of transducer elements.

3. Device as claimed in claim 1, wherein the transducer elements of each group are arranged in alternate fashion so that the total surface occupied by the elements of each group is substantially identical.

4. A device for generating ultrasonic waves focused in one focal point, having reduced negative waves, comprising a plurality of transducer elements of piezoelectric type arranged on a support means for focusing at one focal point, wherein said transducer elements are divided into a least fire and second groups of transducer elements having first and second resonance frequencies, respectively, wherein the resonance frequency of said first group differs form the resonance frequency of said second group, wherein the support means is constituted by a circular dome, wherein all the transducer elements of the different groups are at the same distance from the focal point, called focal distance, which is preferably equal to the radius of curvature of the dome, and wherein one of the at least first and second groups constitutes a reference group activated at a reference time and the other one of the at least first and second groups is activated at a different activation time with respect to the reference group, the time difference being given by the following formula:

$$\Delta t = \lambda / 4 \, V$$

in which t is a time difference of activation between the reference group and the other group, V is the ultrasonic speed in the medium filling the dome, generally constituted by water, and λ is the wavelength at the resonance frequency of the group being activated at the different activation time relative to the reference group, such that the principal positive ultrasonic waves produced by each group are added and the positive and negative secondary ultrasonic waves are at least partly cancelled out.

5. The device of claim 4, wherein the time difference of activation results from a delayed activation of the other group in relation to the reference group.

6. The device of the claim 4, wherein the time difference of activation results from an advanced activation of the other group in relation to the reference group.

7. A device for generating ultrasonic waves focused in one focal point, having reduced negative waves, comprising a plurality of transducer elements of piezoelectric type arranged on a support means for focusing at one focal point, wherein said transducer elements are divided into at least first and second groups of transducer elements having first and second resonance frequencies, respectively which resonance frequencies are different, wherein the support means is constituted by a circular dome, and wherein the distance between the front face of the transducer elements of a given group and the focal point is different from the distance between the front face of the transducer elements of the other groups and the focal point, the electric activation of all the groups being simultaneous, such that the maximum pressure peaks of said at least first and second groups coincide, and the positive and negative secondary ultrasonic waves are at least partly cancelled out.

8. Device as claimed in claim 1, wherein said device comprises a third group of transducer elements of which the resonance frequency is equal or substantially equal to four times the resonance frequency of the first group of transducer elements.

9. Device as claimed in claim 1, wherein the resonance frequency of the transducer elements of the first group is equal to 0.5 MHz.

10. In an apparatus for extracorporeal lithotripsy or for the destruction of particular tissues, the improvement comprising:
a device for generating ultrasonic waves focused in one focal point, having reduced negative waves, comprising a plurality of transducer elements of piezoelectric type arranged on a support means for focusing at one focal point where an object to be destroyed is placed, wherein said transducer elements are divided into at least first and second groups of transducer elements having first and second resonance frequencies, respectively, which resonance frequencies are different, and wherein the second group of transducer elements has a resonance frequency which is equal or substantially equal to a multiple or a submultiple of the resonance frequency of the transducer elements of the first group such that the principal positive ultrasonic waves produced by each group are added and the positive and negative secondary ultrasonic waves are at least partly cancelled out.

11. The device as claimed in claim 10, wherein the resonance frequency of the second group of transducer elements is equal or substantially equal to twice the resonance frequency of the first group of transducer elements.

12. The device as claimed in claim 10, wherein the transducer elements of each group are arranged in alternate fashion so that the total surface occupied by the elements of each group is substantially identical.

13. The device as claimed in claim 10, wherein said device comprises a third group of transducer elements of which the resonance frequency is equal or substantially equal to four times the resonance frequency of the first group of transducer elements.

14. The device as claimed in claim 10, wherein the resonance frequency of the transducer elements of the first group is equal to 0.5 MHz.

15. In an apparatus for extracorporeal lithotripsy or for the destruction of particular tissues, the improvement comprising:
a device for generating ultrasonic waves focused in one focal point, having reduced negative waves, comprising a plurality of transducer elements of piezoelectric type arranged on a support means for focusing at one focal point where an object to be destroyed is situated, wherein said transducer elements are divided into at least first and second groups of transducer elements having first and second resonance frequencies, respectively, wherein the resonance frequency of said first group differs from the resonance frequency of said second group, wherein the support means is constituted by a circular dome, wherein all the transducer elements of the different groups are at the same distance from the focal point, called focal distance, which is preferably equal to the radius of curvature of the dome, and wherein one of the at least first and second groups constitutes a reference group activated at a reference time and the other one of the at least first and second groups is activated at a different activation time with respect to the reference group, the time difference being given by the following formula:

$\Delta t = \lambda/4 \, V$ in which $\Delta t$ is a time difference of activation between the reference group and the other group, V is the ultrasonic speed in the medium filling the dome, generally constituted by water, and $\lambda$ is the wavelength at the resonance frequency of the group being activated at the different activation time relative to the reference group such that the principal positive ultrasonic waves produced by each group are added and the positive and negative secondary ultrasonic waves are at least partly cancelled out.

16. In an apparatus for extracorporeal lithotripsy or for the destruction of particular tissues, the improvement comprising:
a device for generating ultrasonic waves focused in one focal point, having reduced negative waves, comprising a plurality of transducer elements of piezoelectric type arranged on a support means for focusing at one focal point where an object to be destroyed is situated, wherein said transducer elements are divided into at least first and second groups of transducer elements having first and second resonance frequencies, respectively, which resonance frequencies are different, wherein the support means is constituted by a circular dome, and wherein the distance between the front face of the transducer elements of a given group and the focal point is different from the distance between the front face of the transducer elements of the other groups and the focal point, the electric activation of all groups being simultaneous, such that the maximum pressure peaks of said at least first and second groups coincide, and the positive and negative secondary ultrasonic waves are at least partly cancelled out.

17. The device of claim 15, wherein the time difference of activation results from a delayed activation of the other group in relation to the reference group.

18. The device of claim 15, wherein the time difference of activation results from an advanced activation of the other group in relation to the reference group.

* * * * *

UNITED STATES PATENT AND TRADEMARK OFFICE
CERTIFICATE OF CORRECTION

PATENT NO. : 5,015,929

DATED : May 14, 1991

INVENTOR(S) : Dominique Cathignol, Genos; Bernard Lacruche, Lyons; Jean-Louis Mestas, Chassieu, all of France.

It is certified that error appears in the above-identified patent and that said Letters Patent is hereby corrected as shown below:

Column 3, line 34, after "water)," insert --and $\lambda$--.

Column 6, line 13, after "water," insert --and $\lambda$--.

Column 7, line 10, change "transDucer" to --transducer--.

Column 7, line 56, change "on" to --in--.

Column 8, line 17, change "a least fire" to --at least first--.

Column 8, line 20, change "form" to --from--.

Signed and Sealed this

First Day of December, 1992

Attest:

DOUGLAS B. COMER

Attesting Officer

Acting Commissioner of Patents and Trademarks